(12) United States Patent
Alasaarela et al.

(10) Patent No.: US 12,414,689 B2
(45) Date of Patent: Sep. 16, 2025

(54) FOCUS MEASURING ARRANGEMENT AND METHOD OF OPHTHALMIC EXAMINATION, AND OPHTHALMIC EXAMINATION APPARATUS AND METHOD

(71) Applicant: OPTOMED PLC, Oulu (FI)

(72) Inventors: Ilkka Alasaarela, Oulu (FI); Kalle Säippä, Oulu (FI); Juha Lipponen, Oulu (FI); Seppo Rönkkö, Oulu (FI)

(73) Assignee: OPTOMED PLC, Oulu (FI)

( * ) Notice: Subject to any disclaimer, the term of this patent is extended or adjusted under 35 U.S.C. 154(b) by 349 days.

(21) Appl. No.: 18/258,524

(22) PCT Filed: Dec. 14, 2021

(86) PCT No.: PCT/FI2021/050874
§ 371 (c)(1),
(2) Date: Jun. 20, 2023

(87) PCT Pub. No.: WO2022/136729
PCT Pub. Date: Jun. 30, 2022

(65) Prior Publication Data
US 2024/0041317 A1    Feb. 8, 2024

(30) Foreign Application Priority Data

Dec. 21, 2020   (FI) ...................................... 20206351

(51) Int. Cl.
*A61B 3/14*    (2006.01)
*A61B 3/00*    (2006.01)
(Continued)

(52) U.S. Cl.
CPC .......... *A61B 3/1025* (2013.01); *A61B 3/0025* (2013.01); *A61B 3/103* (2013.01);
(Continued)

(58) Field of Classification Search
CPC ........... A61B 3/12; A61B 3/14; A61B 3/1025; A61B 3/0025; A61B 3/103; A61B 3/152;
(Continued)

(56) References Cited

U.S. PATENT DOCUMENTS

2011/0007272 A1    1/2011   Sekiguchi et al.
2012/0002167 A1    1/2012   Kondoh
(Continued)

FOREIGN PATENT DOCUMENTS

EP    2243421 A1    10/2010

OTHER PUBLICATIONS

Search Report for FI Application No. 2006351 dated Jun. 9, 2021, 2 pages.
(Continued)

*Primary Examiner* — Mahidere S Sahle
(74) *Attorney, Agent, or Firm* — Nixon & Vanderhye PC

(57) ABSTRACT

A focus measuring arrangement for ophthalmic examination comprises an infrared light source system, which directs infrared light to a pupil of an eye of a person and forms a focusing pattern of the infrared light on a retina. A receiving arrangement apertures receives the infrared light of the focusing pattern from the retina through separate areas of the pupil. An image forming arrangement causes the infrared light passed through the apertures to form an individual image of the focusing pattern for each of the apertures in an image space of the receiving arrangement, the image forming arrangement causing an optical correspondence between the at least two apertures and the separate areas of the pupil. A detecting surface arrangement is located at a non-zero distance behind the at least two apertures and the image forming arrangement in a direction of propagation of the infrared light reflected from the retina for receiving the infrared light passed through the at least two apertures. A
(Continued)

data processing unit forms focusing adjustment information based on locations of illuminated spots of the infrared light of the focusing pattern on the detecting surface arrangement, and outputs the focusing adjustment information for further processing.

15 Claims, 11 Drawing Sheets

(51) Int. Cl.
  *A61B 3/10*  (2006.01)
  *A61B 3/103*  (2006.01)
  *A61B 3/12*  (2006.01)
  *A61B 3/15*  (2006.01)
  *A61B 5/00*  (2006.01)
  *A61B 5/1455*  (2006.01)

(52) U.S. Cl.
  CPC ............... *A61B 3/12* (2013.01); *A61B 3/152* (2013.01); *A61B 5/14555* (2013.01); *A61B 5/6821* (2013.01)

(58) Field of Classification Search
  CPC ....... A61B 3/0075; A61B 3/0091; A61B 3/10; A61B 5/14555; A61B 5/6821
  USPC .............................. 351/206, 211, 214, 246
  See application file for complete search history.

(56) References Cited

U.S. PATENT DOCUMENTS

| | | |
|---|---|---|
| 2012/0069300 A1 | 3/2012 | Kakuuchi |
| 2012/0154748 A1 | 6/2012 | Inoue et al. |
| 2014/0168401 A1 | 6/2014 | De Bruijn et al. |
| 2015/0070655 A1 | 3/2015 | Rossi |
| 2016/0213249 A1 | 7/2016 | Cornsweet et al. |
| 2020/0015677 A1 | 1/2020 | Inoue |
| 2020/0205659 A1 | 7/2020 | Hirose et al. |

OTHER PUBLICATIONS

International Search Report and Written Opinion of the ISA for PCT/FI2021/050874 dated Mar. 22, 2022, 15 pages.

FOCUS MEASURING ARRANGEMENT AND METHOD OF OPHTHALMIC EXAMINATION, AND OPHTHALMIC EXAMINATION APPARATUS AND METHOD

CROSS-REFERENCE TO RELATED APPLICATIONS

This application is the U.S. national phase of International Application No. PCT/FI2021/050874 filed Dec. 14, 2021 which designated the U.S. and claims priority to FI patent application No. 20206351 filed Dec. 21, 2020, the entire contents of each of which are hereby incorporated by reference.

FIELD

The invention relates to a focus measuring arrangement for ophthalmic examination, an ophthalmic examination apparatus, a focus measuring method of ophthalmic examination and an ophthalmic examination method.

BACKGROUND

A typical problem with ophthalmic instruments is how to focus the ophthalmic instrument to patient's eye. The problem is particularly difficult with examination instruments which are used to examine optically portions of the eye behind the iris, such as a fundus cameras. A wrong focus leads to a bad image quality of the retina, for example. Challenges in focusing are caused by a short time period available for focusing, and changes in eye focus i.e. continuous accommodation, for example. Further challenges may be caused by eye disorders such as myopia, hyperopia or astigmatism, or by eye diseases and by eyes operated by laser eye surgery. Hence, an improvement would be welcome.

Patent document US20140168401 presents a system and a method for remote measurement of optical focus. Patent document US20120154748 presents a fundus camera. Patent document US20110007272 presents also a fundus camera. Patent document US20150070655 presents an apparatus and a method for automatic alignment in an optical system and applications. Patent document US20120002167 presents an ophthalmic apparatus. Patent document US20200205659 presents an ophthalmic apparatus and a method for controlling the same. Patent document EP2243421 presents an ophthalmic device.

BRIEF DESCRIPTION

The present invention seeks to provide an improvement in the focusing of the ophthalmic examination instrument to eye.

The invention is defined by the independent claims. Embodiments are defined in the dependent claims.

LIST OF DRAWINGS

Example embodiments of the present invention are described below, by way of example only, with reference to the accompanying drawings, in which FIGS. 1A and 1B illustrate examples of a focus measuring arrangement and an ophthalmic examination apparatus for ophthalmic examination;

DESCRIPTION OF EMBODIMENTS

Figure 1A:
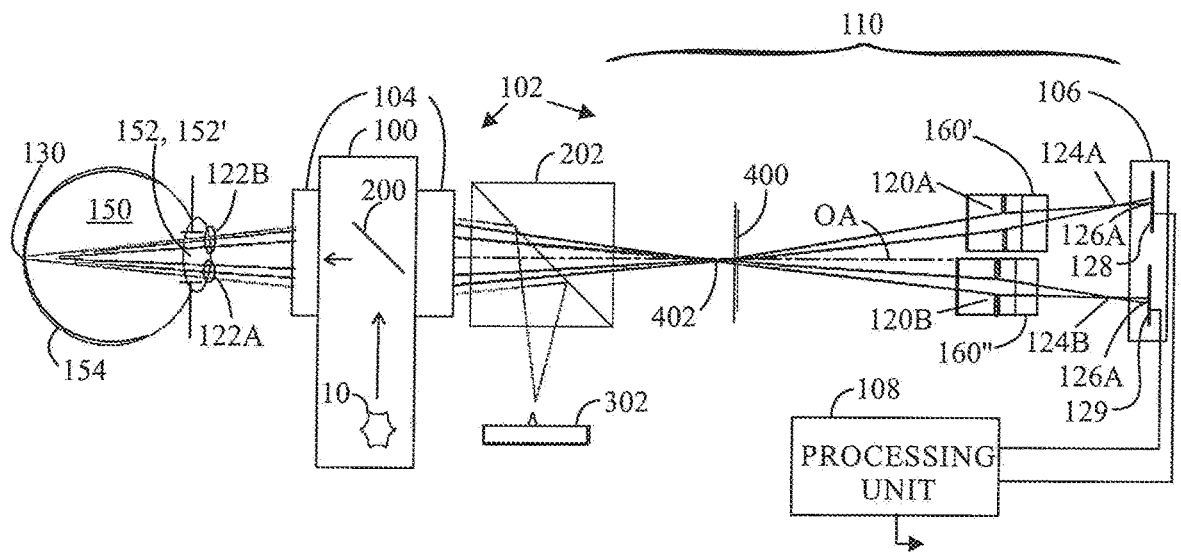

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

First, here are some basic information and working principles of an ophthalmic instrument. The optical instrument comprises at least one image plane, and an imaging optics, where during the use of the ophthalmic instrument, at least a portion of the retina needs to be imaged to the at least one image plane using the imaging optics. Or, the same can be expressed in another way: each of the at least one image plane needs to be imaged on the retina. Here, an image plane should be adjusted be at a detector cell of a digital camera.

The image plane may be in virtual space, i.e. the image formed may be virtual instead of real image. The image plane may not be a physical object, but may be a predetermined surface in space. The image plane may locate outside the ophthalmic instrument, and may be far away or in infinity. The image plane may not be necessarily a plane, but may be a curved surface.

In order to achieve the imaging condition in a sufficient accuracy, the imaging optics needs to be focused to the retina. For example, when using the fundus camera, the fundus camera optics needs to be focused to the retina in order to capture a sharp image of the retina on the camera sensor.

The ophthalmic instrument, which comprises a focus measuring arrangement described in this document, refers to any optical instrument (for example used for examination or treatment of eye) which requires focusing to the retina.

The ophthalmic instrument contains an imaging optics (lenses/mirrors etc.), and the at least one imaging plane which is or is imaged on a camera sensor of a fundus camera. During the use of the ophthalmic instrument, there is a need to focus the imaging optics so that it images at least portion of the retina to the imaging plane using for example ultraviolet (UV), visible (VIS), or near infrared (NIR) wavelengths. The pupil stop of the imaging optics may be imaged, by at least portion of the imaging optics, to a real image, called a first pupil, into between the retina and the ophthalmic instrument. Let us define pupil plane 152' as plane perpendicular to the optical axis of the imaging optics and going through the first pupil.

FIG. 1A illustrates an example of a focus measuring arrangement for ophthalmic examination. In the example of FIG. 1A, the focus measuring arrangement is out-of-focus. In this kind of situation focused individual images 124A, 124B of the focusing pattern 130 that are formed through at least two apertures 120A, 120B are in the imaging space 110 of the receiving arrangement 102 but not on a detecting surface arrangement 106, and that is why in this example, the focused individual images 124A, 124B are in front of the detecting surface arrangement 106. However, focuses of the images 124A, 124B may as well be behind the detecting surface arrangement 106 in an out-of-focus situation. The ophthalmic instrument comprising the focus measuring arrangement is in the examination position or the examining range for examining the eye 150. The focusing pattern 130 may comprise at least one line, at least one point, at least one array of lines or the like without limiting to these. The focusing pattern 130 may increase contrast variations compared to bare retina 154.

The at least one of the at least two apertures 120A, 120B may be located in the image space 110 at a non-zero distance from an optical axis OA of the receiving arrangement 102.

The focus measuring arrangement comprises an infrared light source system 100, which directs infrared light to a pupil 152 of an eye 150 of a person 156 when it is within an examining range from the eye 150. Note that the pupil plane 152' is at the pupil 152 or at least approximately at the pupil 152 when the ophthalmic instrument is focused and ready for the examination of the eye 150. The infrared illumination may be mostly or fully invisible to the eye 150, so that it does not disturb the eye 150 during the measurement of focus and during the examination. For example, the most of the power of the infrared illumination may be between 700 nm and 1000 nm spectral wavelength range. The infrared illumination may also contain some power in the visible spectral region, i.e. between 400 and 700 nm wavelength.

In an embodiment, the infrared light source system 100 may comprise a light source 10, which outputs the infrared light with the focusing pattern 130 (see FIGS. 1A, 1B, 3 and 4).

The infrared light source 100 also forms the focusing pattern 130 of the infrared light on a retina 154 of the eye 150 (the focusing patterns 130 are illustrated in FIGS. 7A to 7D). In an embodiment, the infrared light source system 100 may comprise a first beam splitter 200, which turns at least a portion of the infrared light toward a desired direction. The desired direction is toward the eye 150 when the focus measuring arrangement is within the examining range from the eye 150. The first beam splitter 200 allows at least a portion of the infrared light reflected from the retina 154 pass through toward a detecting surface arrangement 106 in an image space 110 of the receiving arrangement 102. The receiving arrangement 102 comprises optical components that gather light coming from the retina 154 through the pupil 152 of the eye 150, and focus the light on the detecting surface arrangement 106. A part of the optical components may be common to the imaging system 300 of the ophthalmic examination apparatus.

The first beam splitter 200 can be considered common to the infrared light source system 100 or the image forming arrangement 104. The first beam splitter 200 may receive the infrared light and reflect the infrared light at least partly to the pupil 152 of the eye 150, and allow the infrared light reflected from the retina 154 to propagate through at least partly toward the receiving arrangement 102.

The image forming arrangement 104 may comprise one of more optically refractive and/or reflective components which may form a real image or a virtual image. The one of more optically refractive and/or reflective components may comprise at least one lens and/or mirror, which has a curved surface.

The focus measuring arrangement comprises a receiving arrangement 102, which in turn comprises at least two apertures 120A, 120B, which receive the infrared light of the focusing pattern 130 from the retina 154 through separate areas 122A, 122B of the pupil 152. This makes the receiving arrangement 102 to operate in a non-telecentric manner. They may be at the same or a different distance from the detecting surface arrangement 106.

The focus measuring arrangement also comprises an image forming arrangement 104 in the receiving arrangement 102, at least some part of which causes the infrared light passed through the at least two apertures 120A, 120B to form the individual images 124A, 124B of the focusing pattern 130 for each of the at least two apertures 120A, 120B in the image space 110 of the receiving arrangement 102. Only a single the individual image 124A, 124B is formed through one of the apertures 120A, 120B, and there is only one individual image 124A, 124B per a single aperture 120A, 120A. The image forming arrangement 104 additionally causes an optical correspondence between the at least two apertures 120A, 120B and the separate areas 122A, 122B of the pupil 152. That is, at least a part of the image forming arrangement 104 causes the optical correspondence. The optical correspondence may mean that the image forming arrangement 104 forms images of the at least two apertures 120A, 120B on, at or directly adjacent to the pupil 152 of the eye 150, the images being the areas 122A, 122B. The images may be formed, in practice and/or in theory, which makes the areas 122A, 122B and the apertures 120A, 120B have the optical correspondence. The image forming arrangement 104 comprises at least one optical component which can form a real image, the optical component being a lens or a mirror, for example.

The focus measuring arrangement further comprises the detecting surface arrangement 106 located at a non-zero distance behind the at least two apertures 120A, 120B and the image forming arrangement 104 in a direction of propagation of the infrared light reflected from the retina 154.

The detecting surface arrangement 106 has an image plane thereon when the focus measuring arrangement is in-focus. The image of at least portion of the retina 154 is formed on it. The detecting surface arrangement 106 may comprise a matrix sensor such as a complementary metal oxide semiconductor (CMOS) or charge coupled device (CCD) sensor. The detecting surface arrangement 106 may also be a reticle, a slit or an input head of an optical fiber or cable.

In an embodiment, the detecting surface arrangement 106 may comprise only one detecting surface 128 (see FIG. 2A), which may be common to the infrared light from the at least two apertures 120A, 120B for receiving the infrared light passed through the at least two apertures 120A, 120B.

In an embodiment, the detecting surface arrangement 106 may comprise a number of detecting surfaces such that the number of detecting surfaces is smaller than a number of at least two apertures 120A, 120B, and each of the detecting surfaces receives the infrared light from at least one of the at least two apertures 120A, 120B (not illustrated in Figures).

In an embodiment, the detecting surface arrangement 106 may comprise at least two detecting surfaces 128, 129, each of which receives the infrared light from a single aperture of the at least two apertures 120A, 120B. In that manner, there is one to one correspondence between the apertures 120A, 120B and the detecting surfaces 128, 129.

The focus measuring arrangement finally comprises a data processing unit 108, which forms focusing adjustment information based on locations $(X_A, Y_A)$, $(X_B, Y_B)$, $(X_C, Y_C)$ of illuminated spots 126A, 126B of the infrared light of the focusing pattern 130 on the detecting surface arrangement 106. The data processing unit 108 then outputs the focusing adjustment information for further processing.

In an embodiment, the data processing unit 108 may determine locations $(X_A, Y_A)$, $(X_B, Y_B)$, $(X_C, Y_C)$ of centers of the illuminated spots 126A, 126B, 126C. In an embodiment, the data processing unit 108 may determine locations $(X_A, Y_A)$, $(X_B, Y_B)$, $(X_C, Y_C)$ of centers based on image processing.

FIG. 1A also shows an examination detector cell 302 of an imaging system 300 of an ophthalmic examination apparatus for which focusing adjustment information is computed. The ophthalmic instrument comprises both the focus measuring arrangement and the ophthalmic examination apparatus. The examination detector cell 302 has an optically determined relation with respect to the detecting surface arrangement 106. They may be simultaneously in-focus, but alternatively they do not need to be simultaneously in-focus. It is the locations $(X_A, Y_A)$, $(X_B, Y_B)$, $(X_C, Y_C)$ of the illuminated spots 126A, 126B of the focusing pattern 130 on the detecting surface arrangement 106 that have a relation to the focus of the examination detector cell 302 of an imaging system 300 of an ophthalmic examination apparatus.

Figure 1B:
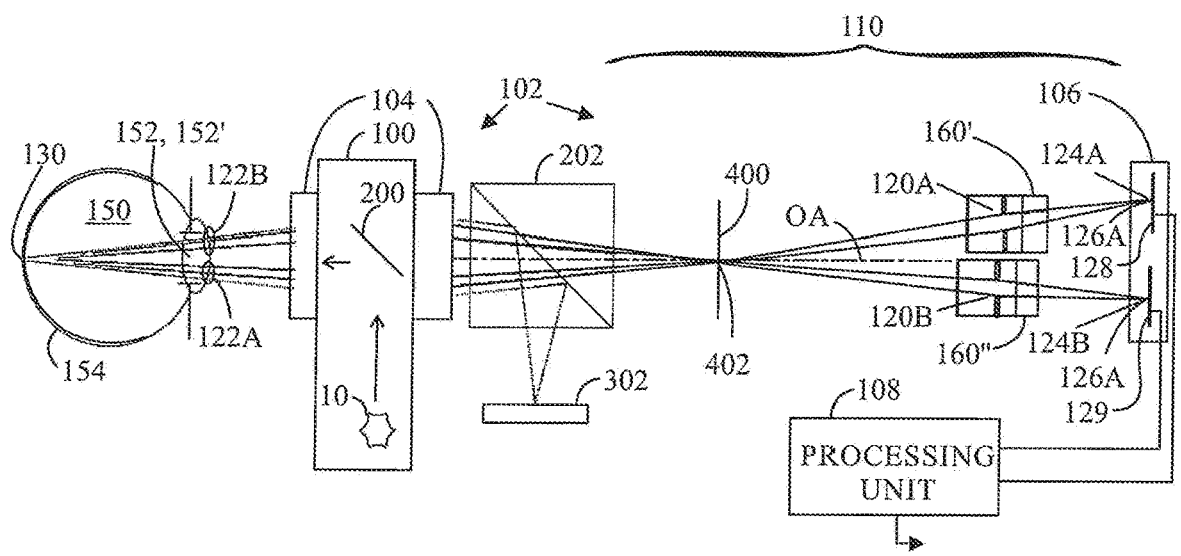

In the example of FIG. 1B, the focus measuring arrangement is in-focus or the spots are in locations $(X_0, Y_0)$ which correspond to a state where the retina 154 is in-focus on the examination detector cell 302. In this kind of situation properly focused individual images 124A, 124B of the focusing pattern 130 may be formed through at least two apertures 120A, 120B on the detecting surface arrangement 106. In this example, the light, which may be visible light and reflected from the retina 154, may also be in-focus at the examination detector cell 302.

The focusing may be performed with the focus measuring arrangement in the following manner.

A) The ophthalmic instrument is brought in such position i.e. examination position with respect to the eye 150 that when illumination of the infrared light source 100 is on, the focusing pattern 130 reflected from the retina 154 is imaged, in-focus or out-of-focus, to the detecting surface arrangement 106. This position is within the examination range of the ophthalmic instrument.

B) The infrared light source 100 forms the focusing pattern 130 on the retina 154. The focusing pattern 130 may contain illuminated features, i.e. contrast differences, on the retina 154, or figures or contrast differences defined by structured illumination (see examples of FIGS. 7A to 7D). The images of the focusing pattern 130 are then captured by the detecting surface arrangement 106. The images may at least initially be out-of-focus before a focus adjustment.

C) Then a predetermined algorithm is used (which depends on the used arrangement) for calculating the required focus shift from the captured images of the focusing pattern 130.

D) The ophthalmic instrument is focused by the required amount in order to get the image of the retina 154 focused on the examination detector cell 302.

E) The focusing process of steps A) to D) or B) to D) may be repeated, if needed.

Figure 2A:
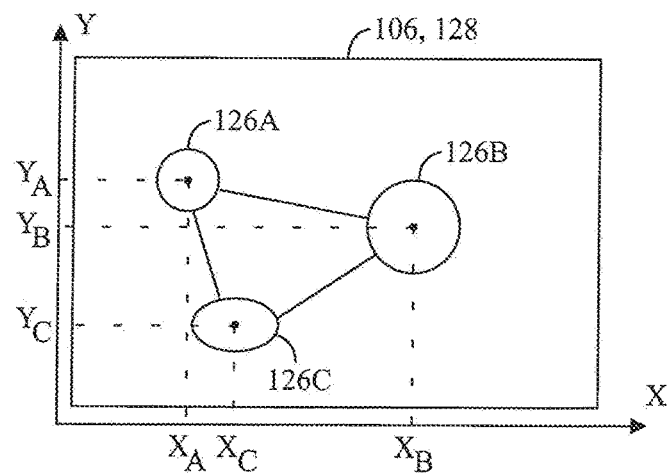
FIG. 2A illustrates an example of three illuminated spots on a single detecting surface arrangement.

FIG. 2A illustrates an example of three illuminated spots 126A, 126B and 126C on the on the detecting surface arrangement 106, which is in this example a single detecting surface 128. The scale of the coordinate system is arbitrary in FIG. 2A. The spots 126A, 126B may be blurred or sharp. In an embodiment, the data processing unit 108 may form the focusing adjustment information based on a geometric characteristic of the at least two illuminated spots 126A, 126B, 126C on the detecting surface arrangement 106, the geometric characteristic being a function that relates to a deviation with respect to a state where the focus measuring arrangement is in-focus and/or the state where the retina 154 is in-focus on the examination detector cell 302.

The geometric characteristic refers to locations $(X_A, Y_A)$, $(X_B, Y_B)$, $(X_C, Y_C)$ of the illuminated spots 126A, 126B, 126C with respect to each other, while a certain locations $(X_{A0}, Y_{A0})$, $(X_{B0}, Y_{B0})$, $(X_{C0}, Y_{C0})$ of them may be used as a reference, on one or more detecting surfaces 128, 129. The locations $(X_A, Y_A)$, $(X_B, Y_B)$, $(X_C, Y_C)$ and/or a shape or form formed by the locations $(X_A, Y_A)$, $(X_B, Y_B)$, $(X_C, Y_C)$ of the illuminated spots 1206A, 126B, 126C and its change can be determined mathematically in the data processing unit 108.

If a plurality of the more detecting surfaces 128, 129 are used, they have fixed or known locations with respect to each other. The illuminated spots 126A, 126B, 126C form a constellation (see line connecting the spots in FIG. 2A) that deterministically varies if a total refraction power of the eye 150 and the focus measuring arrangement varies. Typically the refraction of the eye 150 varies temporally and/or person by person 156 and the variation of the refraction can be monitored with the geometric characteristic of the illuminated spots 126A, 126B, 126C on the detecting surface arrangement 106. Only one configuration of the varying constellation the illuminated spots 126A, 126B, 126C corresponds to a proper focus, where an image of the retina 154 is in-focus, for the ophthalmic examination apparatus. The geometric characteristic can be used to identify the state of focus in a deterministic and recognizable manner.

Figure 2B:
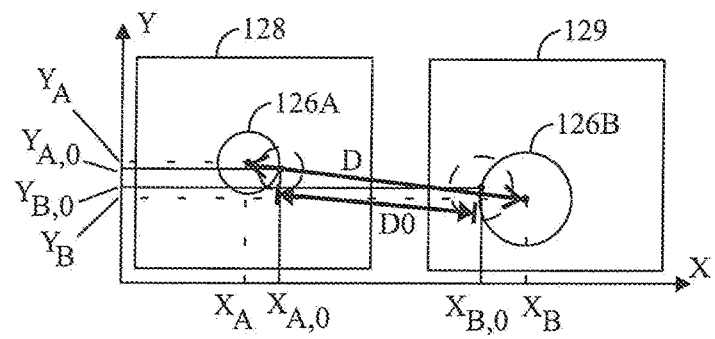
FIG. 2B illustrates an example of two illuminated spots on separate detecting surfaces of the detecting surface arrangement.

In an embodiment an example of which is illustrated in FIG. 2B, the geometric characteristic may refer to at least one distance D between the at least two illuminated spots 126A, 126B on the detecting surface arrangement 106. In this example the detecting surface arrangement 106 comprises two detecting surfaces 128, 129. The distance D may vary depending of the refraction thus revealing the need of the adjustment of focus. In this example, no focus has been reached and the dashed circles show the situation where focus has been reached. Hence, the dashed circles illustrate a reference characteristic linked to a proper focus.

The location difference of the illuminated spots 126A, 126B, 126C may be calculated by various methods. For example, a cross-correlation between the images of the focusing pattern 130 on the detecting surface arrangement 106 and the reference may be calculated, and determining the location shift between the images and the reference that gives a highest correlation. That can be calculated for example by determining locations where a derivative or a gradient of the cross-correlation is approximately zero or crosses zero.

The location and/or geometric difference may also be calculated for example by pattern recognition.

In general, the data processing unit 108 forms the focusing adjustment information based on a comparison between the locations $(X_A, Y_A)$, $(X_B, Y_B)$, $(X_C, Y_C)$ of the at least two illuminated spots 126A, 126B and a reference $(X_{A0}, Y_{A0})$, $(X_{B0}, Y_{B0})$, the reference correspond to the state where the retina 154 is in-focus on the examination detector cell 302.

In an embodiment, the data processing unit 108 may form the focusing adjustment information based on a comparison between the geometric characteristic of the at least two illuminated spots 126A, 126B and the reference characteristic, which corresponds to the state of being in-focus. The state of being in-focus may refer to the state where the retina 154 is in-focus on the examination detector cell 302. The data processing unit 108 may include, in the focusing adjustment information, data on a property of the deviation from the reference characteristic i.e. a deviation from a proper focus. The property of the deviation may comprise one of the following: the reference characteristic differs in one manner from the geometric characteristic of the at least two illuminated spots 126A, 126B, 126C and the reference characteristic differs in an opposite manner from the geometric characteristic of the at least two illuminated spots 126A, 126B. The constellation of the illuminated spots 126A, 126B, 126C may be too large or too small with respect to that of the reference characteristic. In a simpler case, the distance D of the illuminated spots 126A, 126B may be too large or too small with respect to that of the reference characteristic. The difference between the geometric characteristic and the reference characteristic may vary according to linear or non-linear function with respect to the variation of the refraction. The function may be monotonic in the used diopter range. Some examples of such functions are linear equation, or polynomial-function. The function may be piecewise linear or piecewise polynomial function, too.

In an embodiment, the data processing unit 108 may form the focusing adjustment information based on a comparison between the at least one distance D between the at least two illuminated spots 126A, 126B and a reference distance D0, which corresponds to the state where the retina 154 is in-focus on the examination detector cell 302. Then the data processing unit 108 may include, in the focusing adjustment information, data on a direction of the deviation, the direction of the deviation comprising one of the following: the reference distance D0 is larger than the at least one distance D between the at least two illuminated spots 126A, 126B and the reference distance D0 is smaller than the at least one distance D between the at least two illuminated spots 126A, 126B. Based on this information, the refraction power of the imaging system 300 of the ophthalmic examination apparatus can be increased or decreased for forming an image of the retina 154 that is in-focus on the examination detector cell 302.

Figure 3:
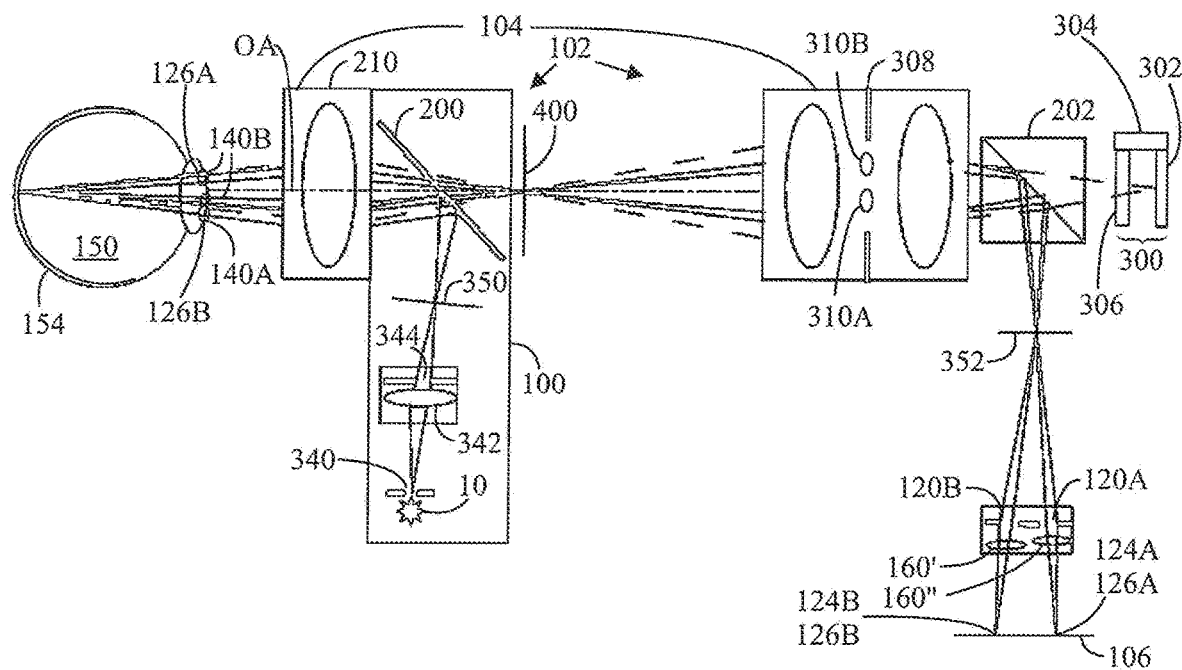
FIG. 3 illustrates an example of the focus measuring arrangement where focusing spots are directed to an eye with a beam splitter.
Figure 5:
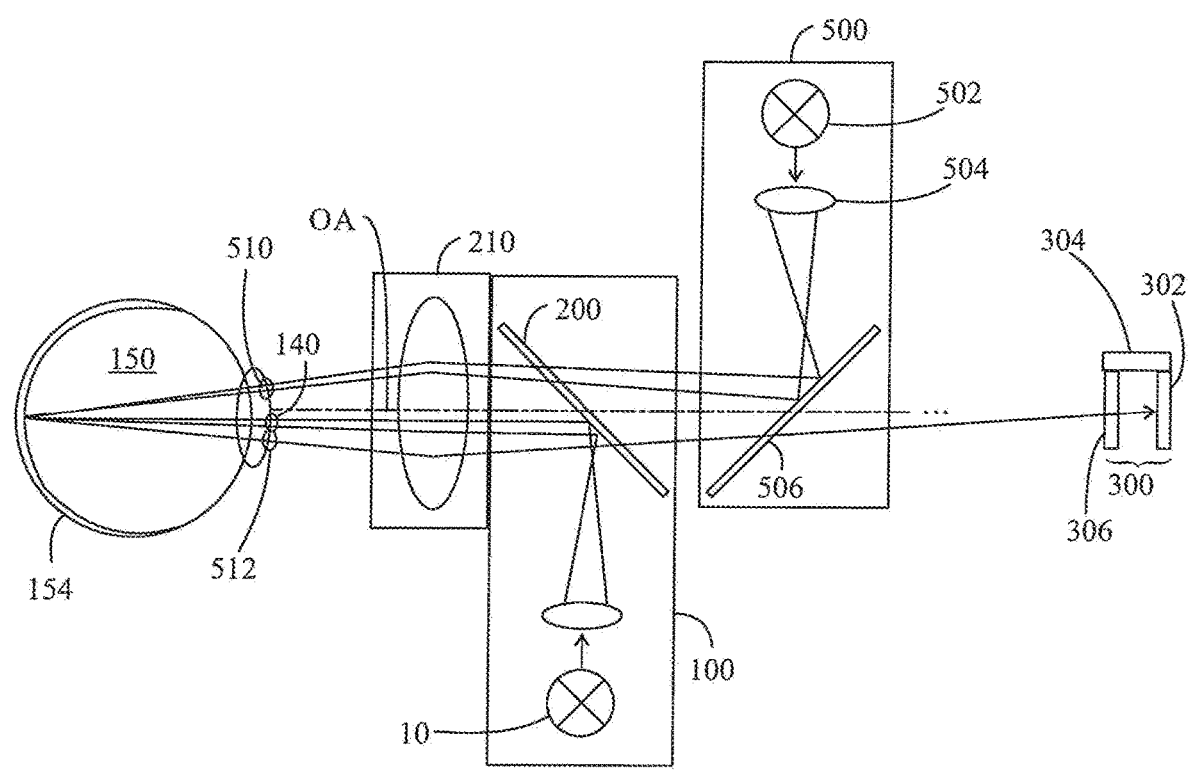
FIG. 5 illustrates an example of the ophthalmic examination apparatus.

In an embodiment an example of which is illustrated in FIGS. 3 and 5, the infrared light source system 100 may direct the infrared light to the retina 154 through at least one sub-section 140, 140A, 140B of the pupil 152 of the eye 150. The receiving arrangement 102 receives the infrared light reflected from the retina 154 through at least two areas 122A, 122B of the pupil 152 of the eye 150. The at least one sub-section 140, 140A, 140B and the at least two areas 122A, 122B may be non-overlapping or at least separate and at least almost non-overlapping.

In an embodiment an example of which is illustrated in FIG. 3, the receiving arrangement 102 may comprise a second beam splitter 202. The second beam splitter 202 may perform one of the following: reflect the at least a part of the infrared light reflected from the retina 154 to the at least two apertures 120A, 120B (see FIGS. 3, 4), and allow at least part of the infrared light reflected from the retina 154 to pass through to the at least two apertures 120A, 120B (see FIGS. 1A, 1B).

In an embodiment an example of which is illustrated in FIG. 3 the infrared light source system 100 may comprise a source aperture 340, an imaging component 342 and an imaging aperture 344. The imaging component 343, which may be a lens, for example, forms an image of the source aperture at an image plane 350. Then the image forming arrangement 104 with such as at least one common image forming optical component 210 the forms an image of the source aperture 340 at the retina 154. The source aperture 340 may include the focusing pattern 130. The source aperture 340 may have a fixed structure that has the image of the focusing pattern 130. Additionally or alternatively, the source aperture 340 may comprise a display such as a liquid crystal display, for example. The display may be controlled by the data processing unit 108. Then the focusing pattern 130 may be static or it may vary in size, location on the retina 154, color and/or shape as a function of time and/or a person.

The at least one common image forming optical component 210 may comprise one of more optically refractive and/or reflective components which may form a real image or a virtual image. The one of more optically refractive and/or reflective components may comprise at least one lens and/or mirror, which has a curved surface.

Figure 4:
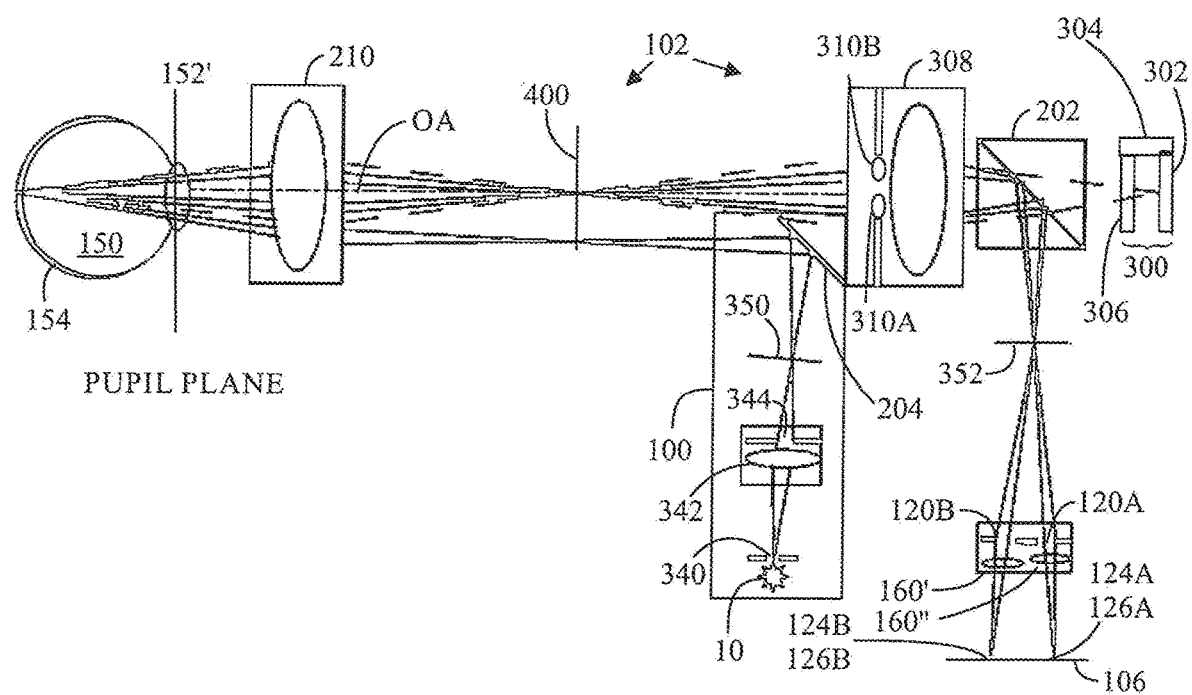
FIG. 4 illustrates another example the focus measuring arrangement where focusing spots are directed to an eye with a mirror.

In an embodiment an example of which is illustrated in FIG. 4, the infrared light source system 100 may comprise a mirror 204. The mirror 204 may receive the infrared light and reflect the infrared light toward the pupil 152 of the eye 150. The mirror 204 may be located at a non-zero distance from the optical axis OA of the receiving arrangement 102 for allowing the infrared light reflected from the retina 154 to propagate without hitting the mirror 204 along the receiving arrangement 102.

In an embodiment, the infrared light source system 100 may direct light to the eye 150 also directly without the mirror 204 or the first beam splitter 200. In such a case, the infrared light source system 100 may be at a location of the mirror 204, for example.

In an embodiment an example of which is illustrated in FIG. 4, the infrared light source system 100 and the receiving arrangement 102 may share the at least one common image forming optical component 210, which may comprise at least one lens, for example. The common image forming optical component 210 may form an intermediate image 400 of the retina 154 in an image plane in front of the second beam splitter 202 (see FIGS. 3, 4). The intermediate image 400 may then be imaged on the examination detector cell 302. FIGS. 1A, 1B illustrate an example where the intermediate image 400 and the image plane are between the second beam splitter 202 and the detecting surface arrangement 106, and the image of the retina 154 is directed with the second beam splitter 202 to the examination detector cell 302 before the intermediate image 400 in the image space 110 of the receiving arrangement 102.

In an embodiment examples of which are illustrated in FIGS. 3 and 4, each of the at least two apertures 120A, 120B may be linked to an individual image forming component 160', 160", which participates in the image formation of the focusing pattern 130 on the detecting surface arrangement 106 and may be considered a part of the receiving arrangement 102 and the image forming arrangement 104. The image forming components 160', 160" may be lenses and the image forming components 160', 160" may locate between the at least apertures 120A, 120B and the detecting surface arrangement 106.

The individual image forming component 160', 160" may comprise one of more optically refractive and/or reflective components which may form a real image or a virtual image. The one of more optically refractive and/or reflective components may comprise at least one lens and/or mirror, which has a curved surface.

In an embodiment, the receiving arrangement 102 may form an intermediate image of the image plane 400 at an image plane 352. Then the individual image forming components 160', 160" form images of the intermediate image at the image plane 352 on the detecting surface arrangement 106. Because the retina 154 is imaged at the image planes 400 and 352, the focusing pattern 130 is also imaged on the detecting surface arrangement 106. When the retina 154 is in-focus at the image planes 400, 352, the focusing pattern 130 is also in-focus at the detecting surface arrangement 106.

FIG. 5 illustrates the ophthalmic examination apparatus, which comprises the focus measuring arrangement explained using FIGS. 1A to 4 and an illuminating unit 500, an imaging system 300 and a focusing actuator 304. In an embodiment, the imaging system 300 may comprise an image forming system 306, which participates in the image formation of the retina 154 on the examination detector cell 302. The image system 306 may comprise at least one lens, for example.

The image forming system 306 may comprise one of more optically refractive and/or reflective components which may form a real image or a virtual image. The one of more optically refractive and/or reflective components may comprise at least one lens and/or mirror, which has a curved surface.

The illumination unit 500 may illuminate the retina 154 through a first region 510 at the pupil 152 of the eye 150, and the examination detector cell 302 may receive the light reflected from the retina 154 through a second region 512 at the pupil 152 of the eye 150. The first region 510 and the second region may be non-overlapping at least at two of the following: the cornea of the eye 150 and the first surface of the crystalline lens of the eye 150, and the second surface of the crystalline lens of the eye 150. In this manner, the Gullstrand's principle may at least almost be fulfilled.

The illuminating unit 500 may comprise an optical radiation source 502, which may output visible light, an optical beam forming component 504 and a third beam splitter 506. Instead of the third beam splitter 506, the illumination unit 500 may comprise a mirror similar to the mirror 204.

The illuminating unit 500 may illuminate the retina 154 of the eye 150. The imaging system 300 comprises the examination detector cell 302, which has the optically determined relation with respect to the detecting surface arrangement 106. In an embodiment, the optically determined relation may mean that the detecting surface arrangement 106 and the examination detector cell 302 are optical conjugates. In an embodiment, the detecting surface arrangement 106 is configured to detect infrared light and the examination detector cell 302 is configured to detect visible light, and the detecting surface arrangement 106 and the examination detector cell 302 are optical conjugates such that when the retina 154 is in-focus on the detecting surface arrangement 106 in the infrared light of the focusing pattern 130, the retina 154 is also in-focus on the examination detector cell 302 in the visible light used in the examination of the eye 150. In this manner, although a proper focus is found, the retina 154 may be in-focus on one of the detecting surface arrangement 106 and the examination detector cell 302 and simultaneously out-of-focus on another of the detecting surface arrangement 106 and the examination detector cell 302 if measured or considered in one wavelength only. But when measured or considered in two different wavelengths that are expressly used for the detecting surface arrangement 106 and the examination detector cell 302 they both can be simultaneously in-focus. The reason for this is that a refraction index of a lens is different for different wavelengths, for example.

The focusing actuator 304 receives the focusing adjustment information, and adjusts the imaging system 300 optically to form a focused image of the retina 154 onto the examination detector cell 302 based on the focusing adjustment information. The focusing actuator 304 may also adjust the at least one common image forming optical component 210. In an embodiment, the focusing actuator 304 may change a distance between at least two lenses of the imaging system 300 and/or the at least one common image forming optical component 210 for causing the image of the retina 154 to be in-focus on the examination detector cell 302. In an embodiment, the focusing actuator 304 may change a refraction index of at least one lens the imaging system 300 and/or the at least one common image forming optical component 210 for causing the image of the retina 154 to be in-focus on the examination detector cell 302. The at least one common image forming optical component 210 may be considered a part of the imaging system 300 but it may also be considered a part of the illumination system providing the visible light to the eye 150, the receiving arrangement 102 and/or the image forming arrangement 104.

The focusing actuator 304 may adjust the focal length of the imaging optics, and/or a distance between the imaging optics and the imaging plane. The adjustment may be performed alternatively, successively or simultaneously. The focal length adjustment may be performed by adjusting distance between at least two optical elements, such as lenses or mirrors, or by at least one electrically tunable lens, such as liquid lens, the refractive index or the curvature of which is changed, for example.

In an embodiment, the focusing actuator 304 may also adjust the individual image forming components 160', 160" for forming the image of the focusing pattern 130 that is in-focus on the detecting surface arrangement 106.

In an embodiment examples of which are illustrated in FIGS. 3 and 4, the second beam splitter 202 may perform one of the following: reflect the at least a part of the illumination reflected from the retina 154 to the examination detector cell 302, and allow at least part of the infrared light reflected from the retina 154 to pass through to the examination detector cell 302.

In an embodiment, the examination detector cell 302 and the detecting surface arrangement 106 are included in the same detector. According to this embodiment, there is only one detector which may both receive the infrared light of the focusing pattern 130 passed through the at least two apertures 120A, 120B and the visible light reflected from the retina 154, the visible light being used for the ophthalmic examination.

In an embodiment examples of which are illustrated in FIGS. 3 and 4, the focus measuring arrangement may comprise a common aperture stop 308, which is common to the examination detector cell 302 and the detecting surface arrangement 106. The at least two apertures 120A, 120B may receive the infrared light of the focusing pattern 130 from the retina 154 through separate sections 310A, 310B of the common aperture stop 308. The separate sections 310A, 310B, in turn, may be non-overlapping. The image forming system 104 may then cause an optical correspondence between the at least two apertures 120A, 120B and the separate sections 310A, 310B of the common aperture stop 308. That is, the image forming system 104 forms, in practice and/or in theory, images of the at least two apertures 120A, 120B on the common aperture stop 308 and the images of the at least two apertures 120A, 120B are the separate sections 310A, 310B. The at least two apertures 120A, 120B and thus the separate sections 310A, 310B may correspond optically the areas 122A, 122B on the pupil 152 of the eye 150.

Figure 6A:
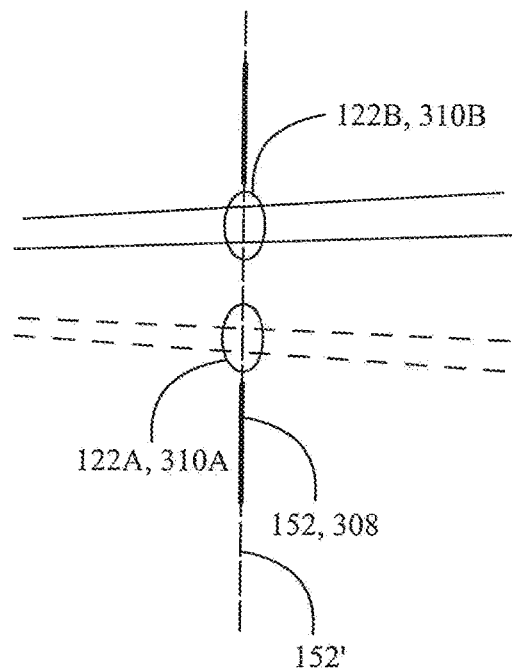
FIGS. 6A and 6B illustrate examples of paths of infrared light of a focusing pattern, the infrared light going through separate sections at an aperture stop.

FIG. 6A illustrates an example of paths of the infrared light of the focusing pattern 130, which goes through the separate sections 310A, 310B at the aperture stop 308. The separate sections 310A, 310B are images 122A, 122B of at least two apertures 120A, 120B at the pupil plane 152' and/or the common aperture stop 308. FIG. 6A illustrates the paths seen in a direction perpendicular to a normal of the pupil plane 152'.

Figure 6B:
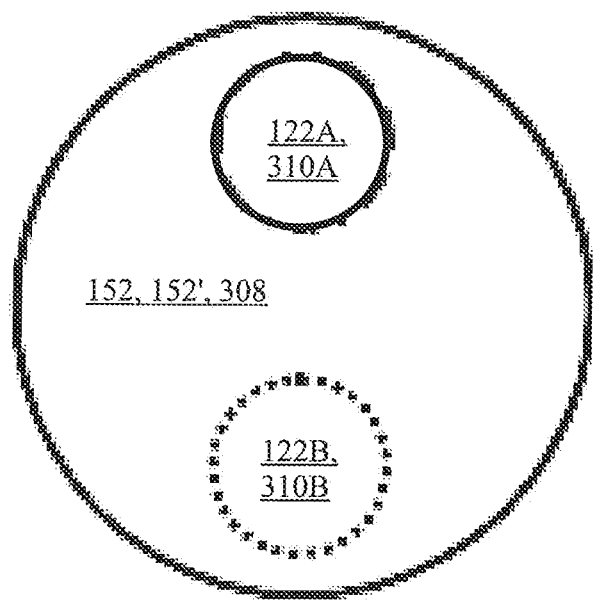
Figure 7A:
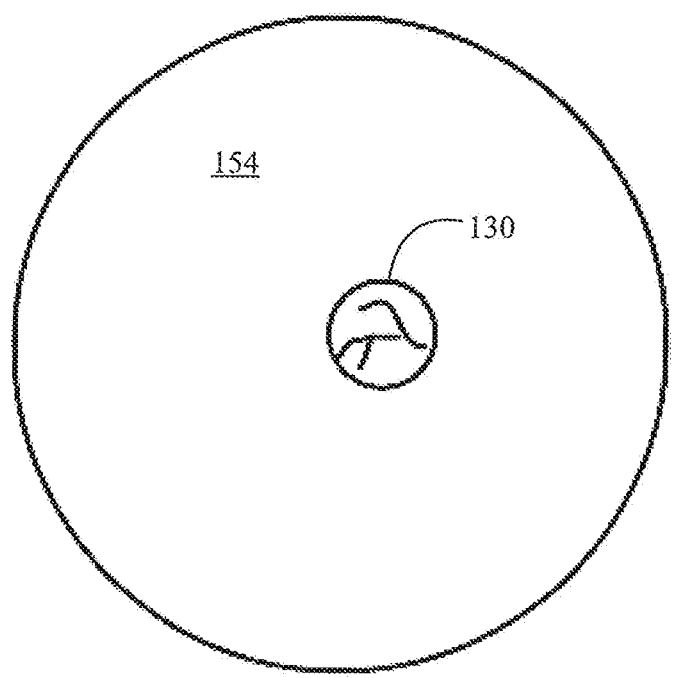
FIG. 7A to 7D illustrate examples of the focusing patterns.
Figure 7B:
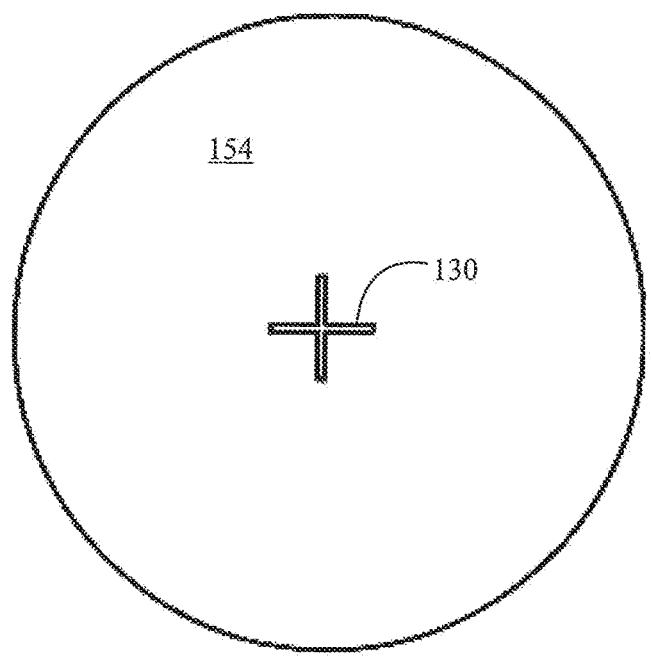
Figure 7C:
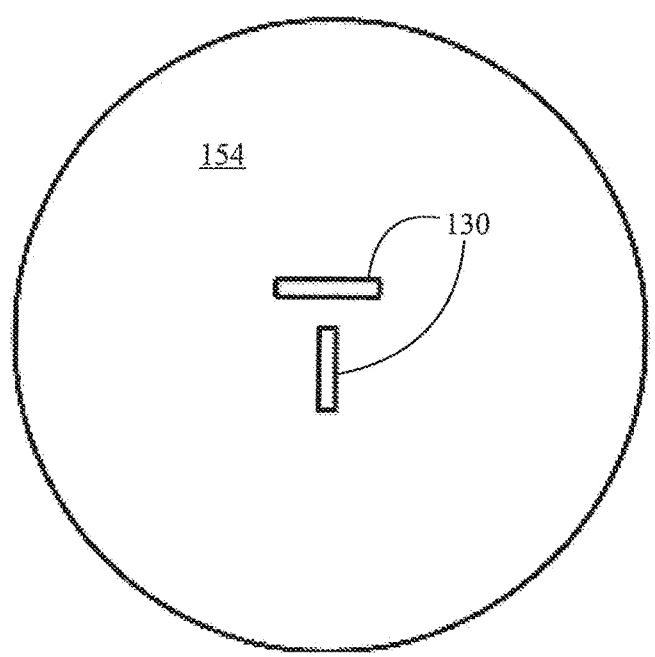
Figure 7D:
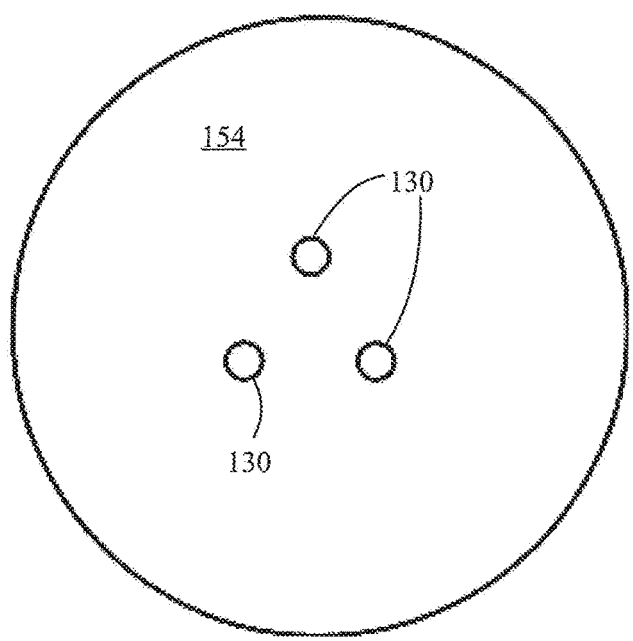

FIG. 6B illustrates an example of paths of the infrared light of the focusing pattern 130, which goes through separate sections 310A, 310B. FIG. 6B illustrates the paths seen in a direction of the normal of the pupil plane 152'.

FIG. 7A to 7D illustrate various shapes of the focusing patterns 310 without limiting to these. The focusing patterns 310 are considered to be on the retina 154 in FIGS. 7A to 7D. Although the focusing patterns 310 are illustrated as sharp images, the focusing patterns 310 may alternatively be more or less blurred.

Figure 8:
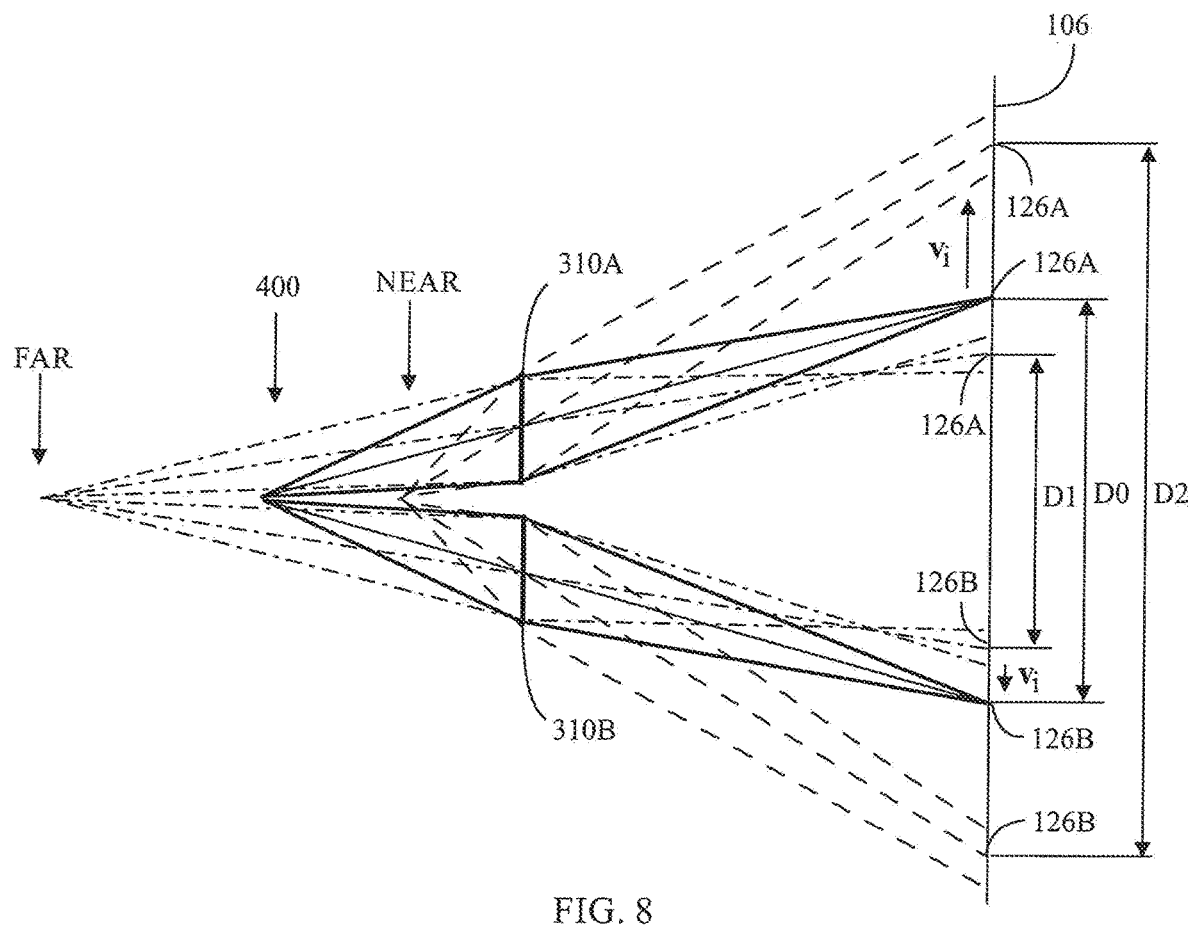
FIG. 8 illustrates examples of rays of infrared light and their locations of illuminated spots on the detecting surface arrangement as a function of a state of focusing (in-focus or out-of-focus)

FIG. 8 illustrates an example of how rays of the infrared light propagate from the intermediate image 402 to the detecting surface arrangement 106. The detecting surface arrangement 106 may be a line sensor or a matrix sensor. Three rays are depicted in each three different focus settings, which shows changes in a position of the intermediate image 402 along the optical axis OA. In the first situation, the intermediate image 402 is formed too far from the detecting surface arrangement 106 and it causes a distance D1 between the two illuminated spots 126A, 126B. In this example of FIG. 8, the illuminated spots 126A, 126B are blurred because they are out-of-focus. In the second situation, the intermediate image 402 is formed at a desired image plane 400 for the detecting surface arrangement 106 and it causes a distance D0 between the two illuminated spots 126A, 126B. In this case the illuminated spots 126A, 126B are focused at the detecting surface arrangement 106. In the third situation, the intermediate image 402 is formed close to the detecting surface arrangement 106 and it causes a distance D2 between the two illuminated spots 126A, 126B. In this example of FIG. 8, the illuminated spots 126A, 126B are blurred because they are out-of-focus in cases of FAR and NEAR.

When the individual images 124A, 124B of the focusing pattern 130 are formed at the detecting surface arrangement 106 in an image space 110 of the receiving arrangement 102, the illuminated spots 126A, 126B are in-focus (see spot at the distance D0 from each other in FIG. 8).

FIG. 9A to 9D illustrate how different shapes focusing patterns 130 can be utilized. FIGS. 9A to 9D show the focusing patterns 130 at the retina 154 on left, and the separate areas 122A, 122B, 122C at the pupil 152 on right. The pictures on right may also be considered or they have a certain correspondence with images of the apertures 120A, 120B, 120C at the pupil 152, at the pupil plane 152', the common aperture stop 308 and/or at the detecting surface arrangement 106. At the pupil 152 and the pupil plane 152' the images are the areas 122A, 122B, 122C. At the common aperture 308 the images are the separate sections 310A, 310B, 310C. At the detecting surface arrangement 106 the images are the illuminated spots 126A, 126B, 126C.

Figure 9A:
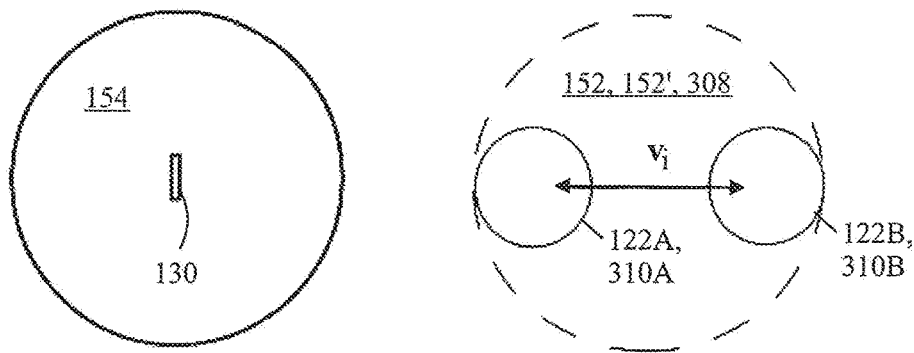
FIG. 9A to 9D illustrate examples of various focusing patterns and their paths at the pupil of the eye and/or the illuminated spots at the detecting surface arrangement.
Figure 9B:
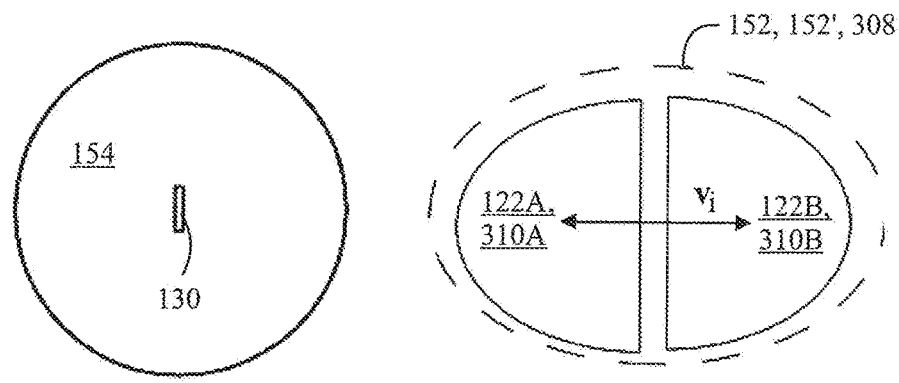
Figure 9C:
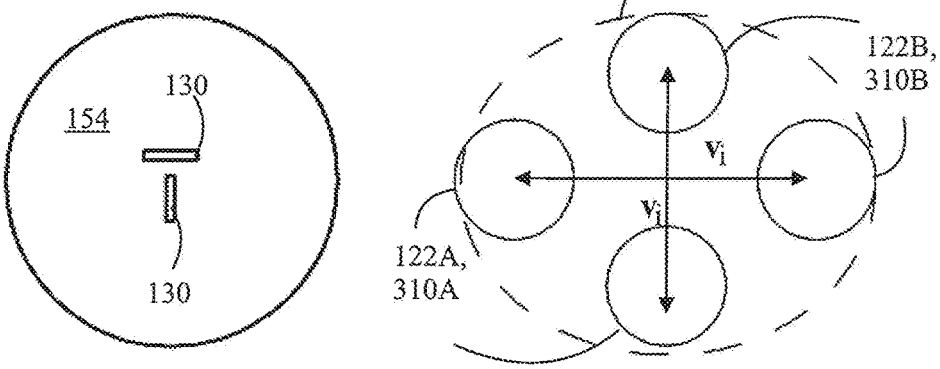
Figure 9D:
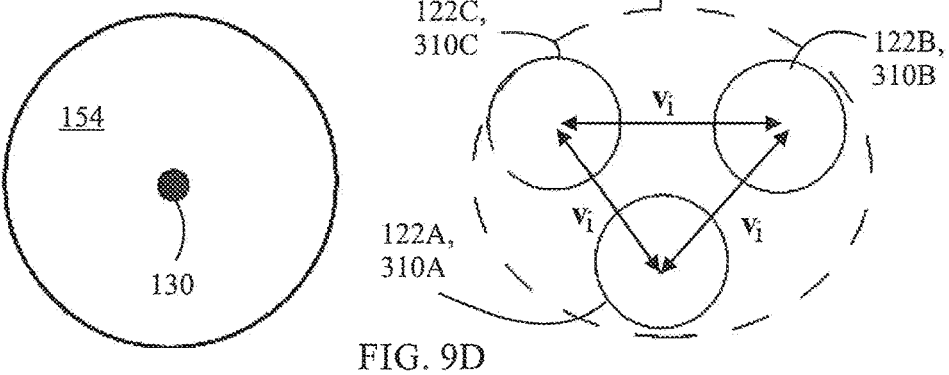
Figure 9E:
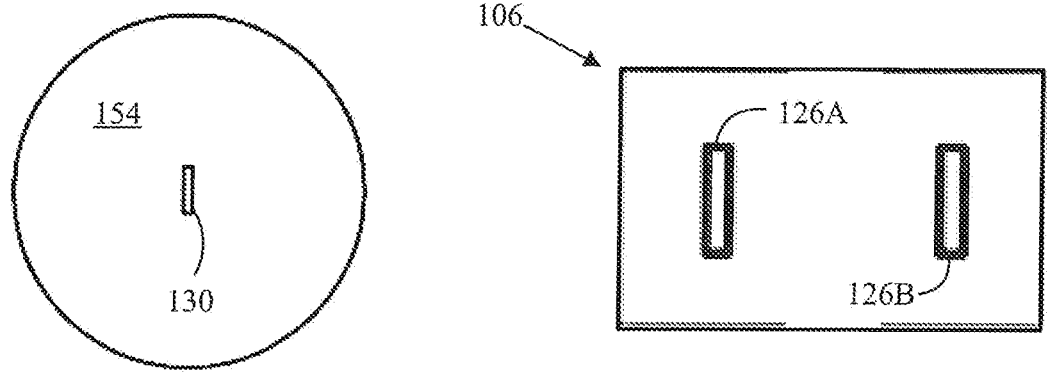
FIGS. 9E to 9G illustrate examples of illuminated spots of various focusing patterns at a detecting surface arrangement and detecting surfaces.
Figure 9F:
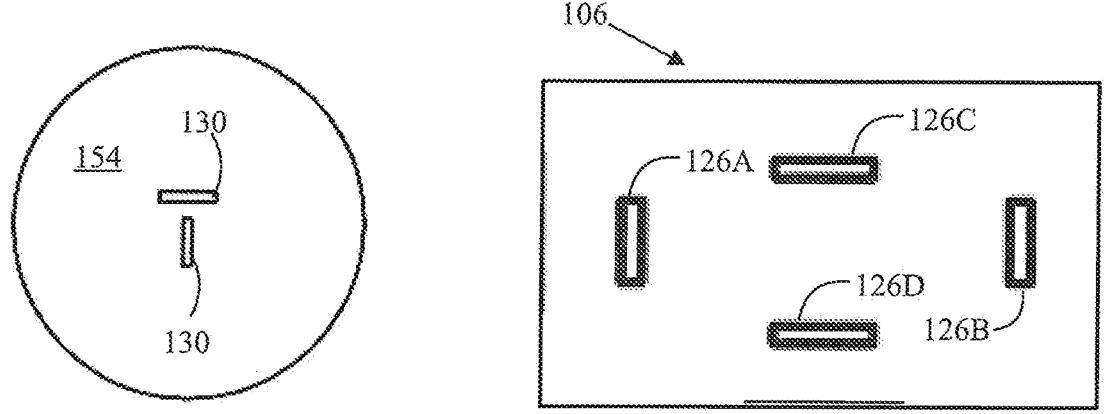
Figure 9G:
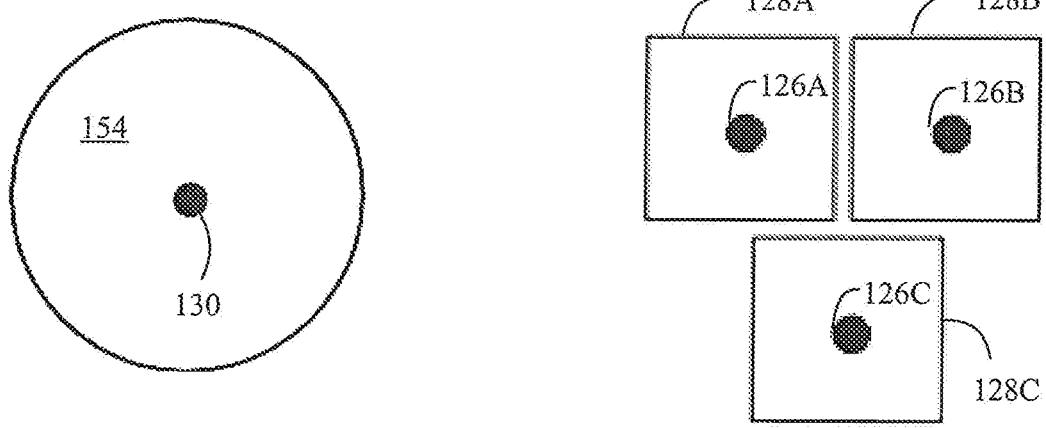

FIGS. 9E to 9G illustrate examples of illuminated spots 126A to 126C of various focusing patterns at the detecting surface arrangement 106 and the detecting surfaces 128A to 128C. FIGS. 9A and 9B correspond to FIG. 9E. In a similar manner FIGS. 9C and 9D correspond to the FIGS. 9F and 9G, respectively.

When an elongated focusing pattern 130, the longitudinal axis of which is vertical, like that in FIG. 9A, is used, the locations are sensitive to the horizontal movement. The beams of infrared light may have a large diameter and the beams may almost completely fill the pupil 152, which is illustrated in FIG. 9B. FIG. 9C illustrates a pair of the focusing patterns 130. One of the focusing patterns may be elongated in a vertical direction, and the infrared light of it may pass the pupil 152 through areas that are side by side at the pupil 152 of the eye 150. Another of the focusing patterns may be elongated in a horizontal direction, and the infrared light of it may pass the pupil 152 through areas where one is above another at the pupil 152 of the eye 150 in the vertical direction. FIG. 9D illustrates an example of the focusing pattern 130 that is a circle. In this example there are three apertures 120A, 120B and 120C images of which are distributed circularly around the pupil 152 of the eye 150 in a non-overlapping manner or at least almost non-overlapping manner. When the detecting surface arrangement 106 has a two-dimensional matrix sensor, the variation of locations of the illuminated spots 126A, 126B, 126C can be monitored in three different directions. It means that the eye astigmatism can be fully measured, i.e. both in its magnitude and axis orientation.

The image forming arrangement 104 images the retina 154 to the detecting surface arrangement 106 such that centroids or the like of images of the separate areas 122A, 122B, which are caused by the at least two apertures 120A, 120B, at the pupil plane 152' and on the detecting surface arrangement 106 deviate from each other. The deviation can be denoted by a vector $v_i$ on the pupil plane 152'. Each beam of the infrared light that travels through one of the separate areas 122A, 122B has typically at least one such a paired beam of the infrared light in another of the separate areas 122A, 122B, that the distance D between the centroids of the pair $|v_i|$ is larger than approximately a quarter of the smallest diameter of the pupil 152, or for example approximately a half of or larger than the smallest diameter of the pupil 152. However, the distance D may be (but not necessarily) smaller than the largest diameter of the pupil 152. The centroids of the images of the separate areas 122A, 122B may locate approximately inside the projection of the pupil 152 on the pupil plane 152'.

The focal shift calculated for a pair of illuminated spots 126A, 126B, for example, may reveal a required focusing need in a direction of the deviation vector $v_i$ corresponding to a pair of illuminated spots 126A, 126B (see FIGS. 8, 9A to 9D). The vector $v_i$ has a magnitude and direction. The direction of the deviation vector $v_i$ may point to left or right, for example. The direction of the deviation vector $v_i$ may point to up or down, for example. More generally, the direction of the deviation vector $v_i$ may point to one direction or to an opposite direction, for example. The ophthalmic instrument may contain at least three pairs of analysis beams formed by at least three apertures similar to the apertures 120A, 120B, whose deviation vectors $v_i$ are substantially non-parallel, such that astigmatism of the eye 150 may be caused to result in different focus shifts between the illuminated spots of the pairs of beams. That information can be used for focusing optimally even the eye 150 having astigmatism.

The focus measuring arrangement may be arranged to form pairs of analysis beams with the apertures 120A, 120B and the deviation vectors $v_i$ based on the illuminated spots 126A, 126B, 126C in any direction where focusing information is needed for the optimal focusing of the ophthalmic examination apparatus.

As the focusing measurement gives not only the direction to which the focus needs to be adjusted, but also the amount of the needed focus adjustment, the described focusing method and adjustment may be performed fast. This may be a useful feature, since the eye 150 under examination tends to get tired quickly and starts drying and moving. One focusing round may be enough for an accurate focus.

The focusing measurement and adjustment may be performed accurately, robustly and in a reliable manner by the following two aspects:

The focus pattern 130 may be arranged to locate in one or more areas on the retina 154, where the most accurate focusing is required for optimal use of the ophthalmic instrument. In other words, the focusing pattern 130 may comprise spots (or for example line segments) in several different positions on the retina 150, and the focus information can be calculated from those different positions at the same time.

The infrared light may be arranged to travel through the front parts of the eye 150 (from crystalline lens to cornea) within such a path, that it optimally takes account the deformations in the person's eye 150 for the ophthalmic instrument operation. For example, in the fundus cameras the infrared light may span the imaging infrared light travelling toward the fundus camera such that the infrared light travelling into the eye 150 experiences the same out-of-focus state and aberrations as the imaging infrared light travelling out of the eye 150. In this manner, the focusing pattern 130 of the infrared light may help in finding the focus with a precise manner.

The robust and accurate operation may be achieved so that the optical beams of the focusing pattern 130 to the detecting surface arrangement 106 are part, i.e. subset, of the beam from the retina 154 to the examination detector cell 302, all the way through the path from the retina 154 to the second beam splitter 202. In that manner, the beams which measure the focus, and the beam which is used to examine the retina 154, experience maximally the same eye accommodation, the same eye aberrations, and the same aberrations and tolerances through the instrument optics. Hence, it may be assumed that the measured focus corresponds the most accurately to the best focus for the examination detector cell 302.

The electric signal levels of the detecting surface arrangement 106 may be amplified with the hardware design if necessary for improving the focus measurement.

Here is the focus measuring arrangement for ophthalmic examination in a nutshell. As the optical beams of the focusing pattern 130 are detected based on the non-telecentric manner, the locations $(X_A, Y_A)$, $(X_B, Y_B)$, $(X_C, Y_C)$ of the spots 126A, 126B (possibly out-of-focus) of the focusing pattern 130 on the detecting surface arrangement 106 depends on the focus of the focus measuring arrangement which has a deterministic relation to the focus of the ophthalmic examination apparatus.

A direction and a magnitude related to the locations $(X_A, Y_A)$, $(X_B, Y_B)$ and/or geometric difference of the (possibly out-of-focus) images of the focusing pattern 130 from a reference $(X_{A0}, Y_{A0})$, $(X_{B0}, Y_{B0})$ can be computed, and determine a geometric difference between the images and the reference. The difference based on the direction and the magnitude, for example, may be understood to be a phase difference. The difference may be determined pairwise of the illuminated spots and one or more distance-value may be formed.

Due to the non-telecentricity at the receiving arrangement 102, a value of the location and/or the geometric difference may be a monotonic function of the required focal shift and it may be used to focus the retina 154 at the detecting surface arrangement 106 and/or the examination detecting cell 302 based on the deviation vector $v_i$ between the at least one pair of the illuminated spots 126A, 126B, 126C. The function may be determined by a calibration of the ophthalmic instrument where the reference is determined when the ophthalmic examination apparatus is in-focus.

The presented solution may be used in many kinds of ophthalmic instruments, such as ophthalmic treatment instruments, for example. This focusing arrangement and method may be suitable to be used in any instrument or device which needs to be in-focus with the eye 150.

An operator may be a person, but the ophthalmic instrument may also be an automatic or autonomous device where the operator is replaced by automation. The operator may also not be present next to the ophthalmic instrument, but may be in a different location and operate the instrument by a remote access.

The ophthalmic instrument can be either a handheld device or a desktop device. The design may be scalable in terms of size. For example, handheld ophthalmic instruments tend to be as small in a physical size as possible and a miniaturized design is more feasible there.

Although a single focusing point is described above, there may be multiple focusing beams, which are targeted to multiple focusing points at the retina 154, so that the focus may be measured from several positions at the retina 154.

That may help determining a best overall focus over the whole field-of-view of the ophthalmic instrument.

The focusing arrangement and method described here can be combined with contrast detection based autofocus methods, for example, such that both of the methods can be used successively, or such that a method, which fits better to the task under action, may be selected.

The ophthalmic instrument may use a wavelength band for the eye examination and a different wavelength band for finding focus for it. For example, the ophthalmic examination apparatus such as a fundus camera may capture images of the retina 154 by using a visible wavelength band and the focus measuring arrangement may use near-infrared wavelengths for the focusing purposes. The required focus difference between the visible and near infrared wavelengths may be known based on calibration, simulation and/or theoretical calculations such that the difference can be taken account when algorithm calculates the required focusing adjustment.

Figure 10:
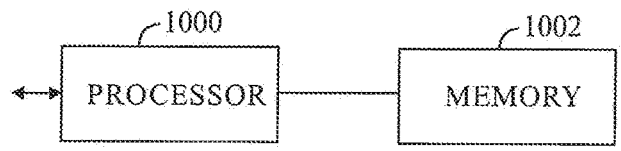
FIG. 10 illustrates an example of a data processing unit.

FIG. 10 an example of the data processing unit 108, which may comprise one or more processors 1000 and one or more memories 1002 including computer program code. The one or more memories 1002 and the computer program code, with the one or more processors 1000 may cause the focus measuring arrangement at least to perform the method illustrated in FIG. 11. In a corresponding manner, the data processing unit 108 be a part of the ophthalmic examination apparatus where the one or more memories 1002 and the computer program code, with the one or more processors 1000 may cause the ophthalmic examination apparatus at least to perform the method illustrated in FIG. 12.

Figure 11:
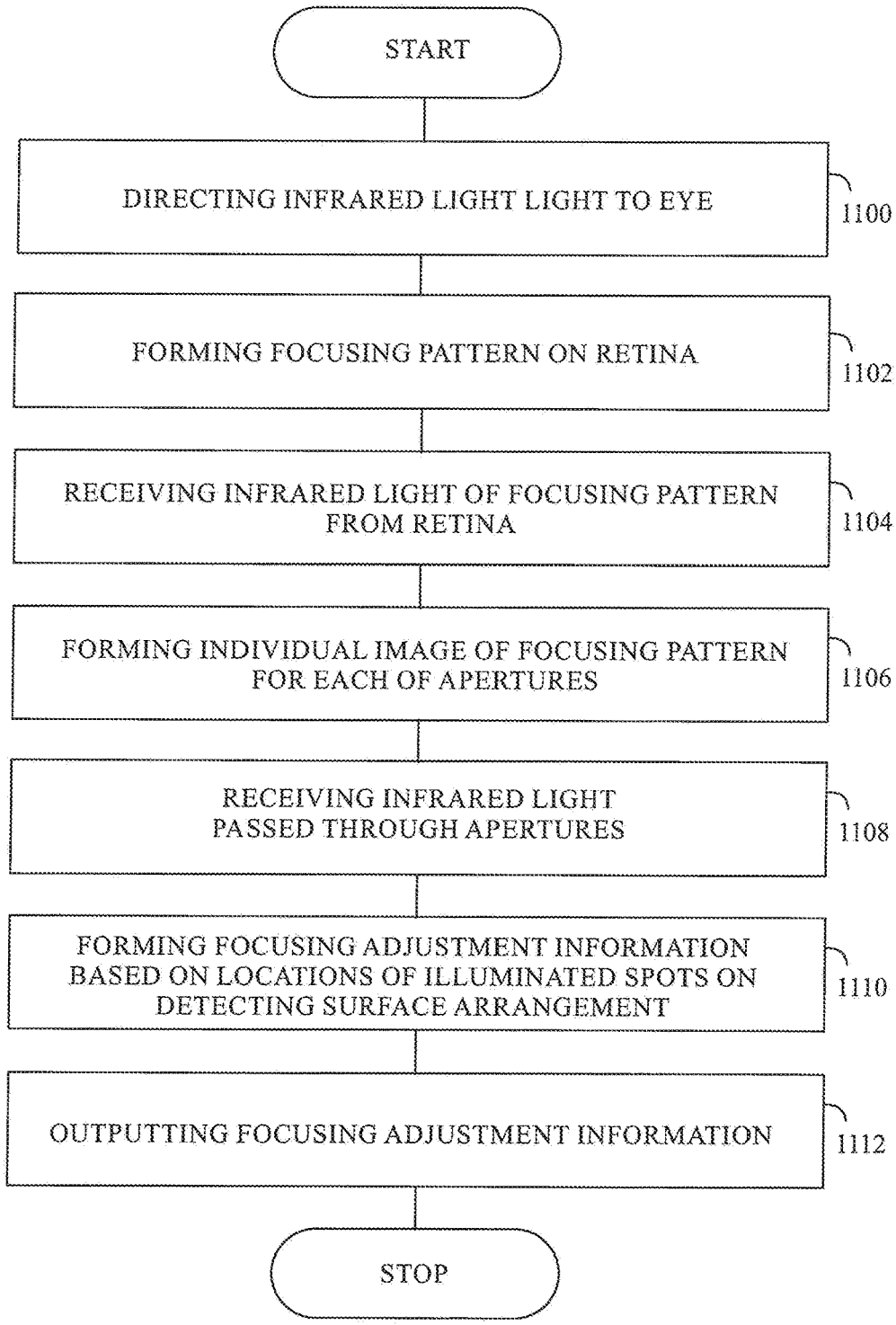
FIG. 11 illustrates an example of a flow chart of a measuring method of ophthalmic examination.

FIG. 11 illustrates the focus measuring method of ophthalmic examination. In step 1100, infrared light is directed to a pupil 152 of an eye 150 of a person with an infrared light source system 100.

In step 1102, a focusing pattern 130 of the infrared light is formed on a retina 154 of the eye 150.

In step 1104, the infrared light of the focusing pattern is received from the retina 154 through separate areas 122A, 122B of the pupil 152 with at least two apertures 120A, 120B of a receiving arrangement 102.

In step 1106, an individual image 124A, 124B of the focusing pattern 130 is formed with an image forming arrangement 104, for each of at least two apertures 120A, 120B, which the infrared light passed through, in an image space 110 of the receiving arrangement 102, while the image forming arrangement 104 causes an optical correspondence between the at least two apertures 120A, 120B and the separate areas 122A, 122B of the pupil 152.

In step 1108, receiving the infrared light passed through the at least two apertures 120A, 120B with a detecting surface arrangement 106 located at a non-zero distance behind the at least two apertures 120A, 120B and the image forming arrangement 104 in a direction of propagation of the infrared light reflected from the retina 104.

In step 1110, focusing adjustment information is formed with a data processing unit 108 based on locations $(X_A, Y_A)$, $(X_B, Y_B)$, $(X_C, Y_C)$ of illuminated spots 126A, 126B, 126C of the infrared light of the focusing pattern 130 on the detecting surface arrangement 106.

In step 1112, the data processing unit 108 outputs the focusing adjustment information for further processing.

Figure 12:
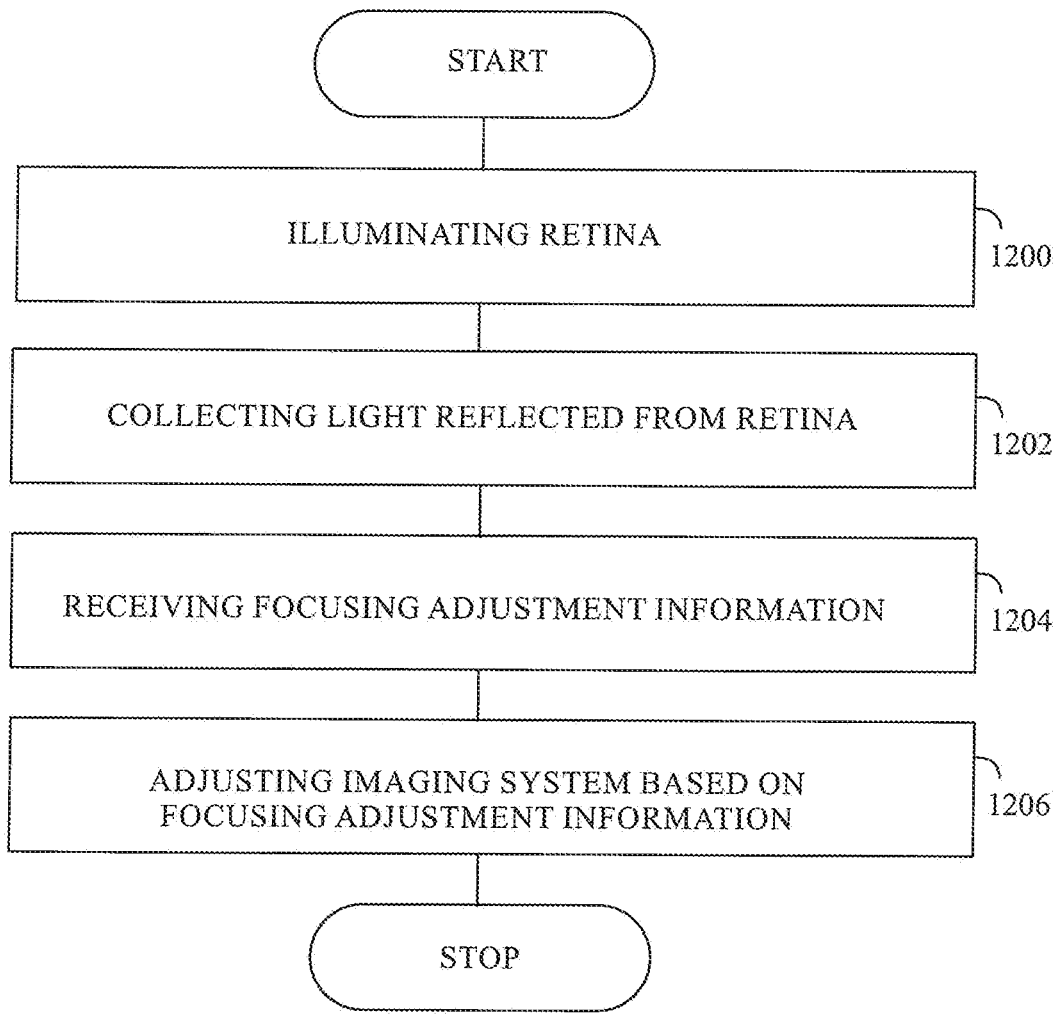
FIG. 12 illustrates of an example of a flow chart of an ophthalmic examination method.

FIG. 12 illustrates the ophthalmic examination method. In step 1200, the focus measuring method of FIG. 11 is performed.

In step 1202, the retina 154 of the eye 150 is illuminated with an illuminating unit 500.

In step 1204, light of illuminating unit 500 reflected from the retina 154 is collected with imaging system 300, which comprises an examination detector cell 302, which has an optically determined relation with respect to the detecting surface arrangement 106.

In step 1206, the focusing adjustment information is received by a focusing actuator 304.

In step 1208, the imaging system 300 is adjusted optically to form a focused image of the retina 154 onto the examination detector cell 302 in response to the focusing adjustment information.

The data processing parts of the methods shown in FIGS. 11 and 12 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

What is presented in this document teaches how to focus the ophthalmic instrument to the eye 150 effectively, and it may result in one or more of the following potential advantages:
faster focusing
more accurate focusing
more accurate focusing in presence of astigmatism in the eye
more reliable focusing
more user friendly focusing.

It will be obvious to a person skilled in the art that, as technology advances, the inventive concept can be implemented in various ways. The invention and its embodiments are not limited to the example embodiments described above but may vary within the scope of the claims.

The invention claimed is:

1. A focus measuring arrangement for ophthalmic examination, which comprises:
an infrared light source system, which is configured to direct infrared light to a pupil of an eye of a person and form a focusing pattern of the infrared light on a retina of the eye, wherein the focus measuring arrangement further comprises
a receiving arrangement, which comprises
at least two apertures, which are configured to receive the infrared light of the focusing pattern from the retina through separate areas of the pupil,
an image forming arrangement, which is configured to cause the infrared light passed through the at least two apertures to form an individual image of the focusing pattern for each of the at least two apertures in an image space of the receiving arrangement, the image forming arrangement being configured to cause an optical correspondence between the at least two apertures and the separate areas of the pupil, and
a detecting surface arrangement located at a non-zero distance behind the at least two apertures and the image forming arrangement in a direction of propagation of the infrared light reflected from the retina for receiving the infrared light passed through the at least two apertures; and a data processing unit, which is configured to form focusing adjustment information based on locations of illuminated spots of the infrared light of the focusing pattern on the detecting surface arrangement, and output the focusing adjustment information for further processing.

2. The focus measuring arrangement of claim 1, wherein the data processing unit is configured to form the focusing adjustment information based on a geometric characteristic of the at least two illuminated spots on the detecting surface arrangement, the characteristic being a function of deviation from a state of being in-focus of the focus measuring arrangement.

3. The focus measuring arrangement of claim 2, wherein the geometric characteristic is at least one distance between the at least two illuminated spots on the detecting surface arrangement, the distance varying as a function of deviation from a state of being in-focus of the focus measuring arrangement.

4. The focus measuring arrangement of claim 2, wherein the data processing unit is configured to form the focusing adjustment information based on a comparison between the geometric characteristic of the at least two illuminated spots and a reference characteristic, which corresponds to the state of being in-focus, and the data processing unit is configured include in the focusing adjustment information data on a property of the deviation, the property of the deviation comprising one of the following: the reference characteristic differs in one manner from the geometric characteristic of the at least two illuminated spots and the reference characteristic differs in an opposite manner from the geometric characteristic of the at least two illuminated spots.

5. The focus measuring arrangement of claim 3, wherein the data processing unit is configured to form the focusing adjustment information based on a comparison between the at least one distance between the at least two illuminated spots and a reference distance, which corresponds to the state of being in-focus, and the data processing unit is configured include in the focusing adjustment information data on a direction of the deviation, the direction of the deviation comprising one of the following: the reference distance is larger than the at least one distance between the at least two illuminated spots is smaller than the at least one distance between the at least two illuminated spots.

6. The focus measuring arrangement of claim 1, wherein the infrared light source system is configured to direct the infrared light to the retina through at least one first sub-section of the pupil of the eye;

the receiving arrangement is configured to receive the infrared light reflected from the retina through at least one second sub-section of the pupil of the eye;

the at least one first sub-section and the at least one second sub-section being non-overlapping.

7. The focus measuring arrangement of claim 1, wherein the receiving arrangement comprises a second beam splitter, which is configured to perform one of the following: reflect the at least a part of the infrared light reflected from the retina to the at least two apertures, and allow at least part of the infrared light reflected from the retina to pass through to the at least two apertures.

8. The focus measuring arrangement of claim 1, wherein each of the at least two apertures is linked to an individual image forming component, which is configured to partici-
pate in an image formation of the focusing pattern on the detecting surface arrangement.

9. An ophthalmic examination apparatus, wherein ophthalmic examination apparatus comprises:

the focus measuring arrangement of claim 1; and an illuminating unit configured to illuminate the retina of the eye;

an imaging system, which comprises an examination detector cell, which has an optically determined relation with respect to the detecting surface arrangement;

a focusing actuator, which is configured to receive the focusing adjustment information, and adjust the imaging system optically to form a focused image of the retina onto the examination detector cell in response to the focusing adjustment information.

10. The apparatus of claim 9, wherein the second beam splitter is configured to perform one of the following: reflect the at least a part of the illumination reflected from the retina to the examination detector cell, and allow at least part of the infrared light reflected from the retina to pass through to the examination detector cell.

11. The apparatus of claim 9, wherein imaging system comprises the image forming system.

12. The apparatus of claim 9, wherein imaging system, which comprises the examination detector cell, which is an optical conjugate to the detecting surface arrangement.

13. The apparatus of claim 9, wherein the focus measuring arrangement comprises a common aperture stop, which is common to the examination detector cell and the detecting surface arrangement, and the at least two apertures are configured to receive the infrared light of the focusing pattern from the retina through separate sections of the common aperture stop, the separate sections being non-overlapping, and the image forming system being configured to cause an optical correspondence between the at least two apertures and the separate sections of the common aperture stop.

14. A focus measuring method of ophthalmic examination, the method comprising directing, with an infrared light source system, infrared light to a pupil of an eye of a person, the method comprising forming a focusing pattern of the infrared light on a retina of the eye;

receiving, with at least two apertures of a receiving arrangement, the infrared light of the focusing pattern from the retina through separate areas of the pupil;

forming, with an image forming arrangement, an individual image of the focusing pattern for each of at least two apertures, which the infrared light passed through, in an image space of the receiving arrangement, while the image forming arrangement causes an optical correspondence between the at least two apertures and the separate areas of the pupil;

receiving, with a detecting surface arrangement located at a non-zero distance behind the at least two apertures and the image forming arrangement in a direction of propagation of the infrared light reflected from the retina, the infrared light passed through the at least two apertures;

forming, with a data processing unit, focusing adjustment information based on locations of illuminated spots of the infrared light of the focusing pattern on the detecting surface arrangement; and outputting, from a data processing unit, the focusing adjustment information for further processing.

15. An ophthalmic examination method, the method further comprising performing the focus measuring method of claim 14; and
- illuminating, with an illuminating unit, the retina of the eye;
- collecting light of illuminating unit reflected from the retina with imaging system, which comprises an examination detector cell, which has an optically determined relation with respect to the detecting surface arrangement;
- receiving the focusing adjustment information by a focusing actuator; and
- adjusting the imaging system optically to form a focused image of the retina onto the examination detector cell in response to the focusing adjustment information.

* * * * *